United States Patent
Naso et al.

(10) Patent No.: US 11,366,090 B2
(45) Date of Patent: Jun. 21, 2022

(54) METHOD FOR THE INACTIVATION AND INACTIVATION TESTING OF XENO ANTIGENS IN FOODS OF ANIMAL ORIGIN, PARTICULARLY FOR MILK AND DERIVATIVES, AND IN FOODS OF PLANT ORIGIN, PARTICULARLY FOR MILK SUBSTITUTES BASED ON SOY AND/OR RICE

(71) Applicant: Biocompatibility Innovation S.R.L., Este (IT)

(72) Inventors: Filippo Naso, Ospedaletto Euganeo (IT); Alessandro Gandaglia, Rubano (IT); Ugo Stefanelli, Padua (IT)

(73) Assignee: Biocompatibility Innovation S.R.L., Este (IT)

( * ) Notice: Subject to any disclaimer, the term of this patent is extended or adjusted under 35 U.S.C. 154(b) by 0 days.

(21) Appl. No.: 16/349,707

(22) PCT Filed: Nov. 14, 2017

(86) PCT No.: PCT/EP2017/079196
§ 371 (c)(1),
(2) Date: May 14, 2019

(87) PCT Pub. No.: WO2018/091460
PCT Pub. Date: May 24, 2018

(65) Prior Publication Data
US 2019/0317069 A1    Oct. 17, 2019

(30) Foreign Application Priority Data
Nov. 16, 2016 (IT) .................. 102016000115523

(51) Int. Cl.
| | |
|---|---|
| A23C 7/04 | (2006.01) |
| A23L 5/20 | (2016.01) |
| G01N 33/02 | (2006.01) |
| G01N 33/50 | (2006.01) |
| G01N 33/04 | (2006.01) |
| G01N 33/08 | (2006.01) |
| G01N 33/12 | (2006.01) |

(52) U.S. Cl.
CPC .............. *G01N 33/04* (2013.01); *A23C 7/04* (2013.01); *A23L 5/20* (2016.08); *G01N 33/025* (2013.01); *A23V 2002/00* (2013.01); *G01N 33/08* (2013.01); *G01N 33/12* (2013.01)

(58) Field of Classification Search
CPC ...... G01N 33/04; G01N 33/025; G01N 33/08; G01N 33/12; G01N 33/50; A23C 7/04; A23L 5/20; A23L 33/00; A23V 2002/00; A61K 39/35
See application file for complete search history.

(56) References Cited

U.S. PATENT DOCUMENTS

2018/0353647 A1* 12/2018 Naso .................. A61L 27/3687

OTHER PUBLICATIONS

Chung et al. ("Removing peanut allergens by tannic acid", Food Chemistry, vol. 134, pp. 1468-1473, published Mar. 21, 2012) (Year: 2012).*
Cursaru et al. ("Investigations on the Oxidation Stability of Biodiesel Synthesized from Different Vegetable Oils", Rev. Chim. (Bucharest), vol. 64, No. 4, pp. 438-441, published 2013) (Year: 2013).*
Si-Yin Chung et al. ("Ferulic acid enhances IgE binding to peanut allergens in Western blots", Food Chemistry, vol. 124, pp. 1639-1642, published 2011) (Year: 2011).*
Woodfolk et al. ("Allergens, sources, particles, and molecules: Why do we make IgE responses?"Allergology International, vol. 64, pp. 295-303, published Jul. 15, 2015). (Year: 2015).*
Commins et al. ("Delay Anaphylaxis to Red Meat in Patients with IgE Specific for Galactose alpha-1,3-Galactose (alpha-gal)", Curr. Allergy Asthma Rep., vol. 13, pp. 72-77, published 2013) (Year: 2013).*

* cited by examiner

*Primary Examiner* — Tracy Vivlemore
*Assistant Examiner* — Nam P Nguyen
(74) *Attorney, Agent, or Firm* — MacMillan, Sobanski & Todd, LLC

(57) ABSTRACT

A method for the inactivation and inactivation testing of xenoantigens in foods of vegetable and animal origin, comprising the following steps: making up a solution with a food of vegetable or animal origin as a solvent and one or more phenolic compounds, polyphenolic compounds and derivatives thereof, comprising phenylpropanoids, as a solute, for the inactivation of at least part of the xenogeneic epitopes from said food, incubating samples of the food of vegetable or animal origin with the addition of an antibody aimed at a xenoantigen epitope that is present in the food, separating the resulting immune complex created owing to the bond between antigen and antibody, preparing a well plate for the E.L.I.S.A. test with coating with xenoantigen epitope, adding, in the wells, supernatant taken from the samples, the supernatant containing the part of antibody that has not bonded with epitopes, a column of wells being adapted to define a reference value that corresponds to the maximum signal between antibody and epitopes, completing the plate with a secondary antibody conjugated with an enzyme, or other molecule, adapted to chromatically highlight any presence of anti-xenoantigen antibody, reading the plate, determining the presence of anti-xenoantigen antibody that has remained free in the solutions of the samples, comparing the absorbance values detected in the reference column with the values in the other columns of samples of the plate.

17 Claims, 3 Drawing Sheets

METHOD FOR THE INACTIVATION AND INACTIVATION TESTING OF XENO ANTIGENS IN FOODS OF ANIMAL ORIGIN, PARTICULARLY FOR MILK AND DERIVATIVES, AND IN FOODS OF PLANT ORIGIN, PARTICULARLY FOR MILK SUBSTITUTES BASED ON SOY AND/OR RICE

This is a national stage application filed under 35 U.S.C. § 371 of international application PCT/EP17/079196, filed under the authority of the Patent Cooperation Treaty on Nov. 14, 2017, published; which claims the benefit of Italy Patent Application No. 102016000115523, filed on Nov. 16, 2016. The entire disclosures of all the aforementioned applications are expressly incorporated herein by reference for all purposes.

The present invention relates to a method for the inactivation and inactivation testing of xenoantigens in foods of vegetable and animal origin.

In particular, the invention relates to a method for inactivating and the inactivation testing of xenoantigens in foods of vegetable and animal origin, in particular of the alpha-Gal epitope, in particular for whole cow's milk, for soy milk and for rice milk, and derivatives, through the use of biological activities identified in phenolic compounds, polyphenolic compounds, or derivatives thereof, including phenylpropanoids, hereinafter referred to for the sake of simplicity with the abbreviation FPF.

To date, over 170 types of foods have been identified as being capable of causing allergy and/or intolerance.

Of such foods, the most common are milk and its derivatives, soya, and red meat, followed by eggs, peanuts, nuts in general, crustaceans and molluscs.

Today, food allergies affect 6% overall of the children and 4% overall of adults living in Europe, Australasia and the USA. Recently, new cases of allergies have come to light which were triggered by the specific intake of red meat or of milk (cow's or goat's milk), which can develop into a series of events ranging from classic reactions such as hives, gastrointestinal disorders, delayed growth in children and systemic anaphylaxis, up to the possible death of the subject.

Such phenomenon is determined by the presence in the foods in question of a specific molecule called alpha-Gal.

This specific allergic form particularly concerns the US and Australian market, to the point where in those countries special surveillance teams have been set up, named respectively "Alpha-Gal National Surveillance" and "TIARA—Tick Induced Allergies Research and Awareness", dedicated to monitoring the phenomenon and offering health education on it.

30% of patients admitted for treatment following the onset of food allergies in the USA are in fact affected by the development of a form of intolerance of and/or allergy to the alpha-Gal molecule.

In Europe similar reactions have been found in Denmark (5.6% of the population), Spain (8.1% of the population), Sweden, Germany, France and Switzerland.

The alpha-Gal molecule is a determining antigenic constituted by two galactose residues bonded to each other by an alpha-glycosidic bond, and it has been found in all mammals except humans and the more advanced primates.

Such molecule is predominantly expressed on glycoproteins and on membrane glycolipids by virtue of the action of an enzyme named alpha-galactosyltransferase.

In its evolution as a consequence of natural mutations, the human race has lost the functionality of this enzyme, by developing antibodies from infancy that are directed against the alpha-Gal antigen and which constitute 1% of all the immunoglobulins in circulation (IgG, IgA, IgM and IgE).

In the milk of mammals (except for humans), the alpha-Gal epitope is present because, in mammary glands, the apical cytoplasm of the secreting elements is eliminated together with the secretion product.

In this manner, in the secreted liquid there are also fragments of cellular membranes exhibiting reactive alpha-Gal xenoantigens that are capable of instigating phenomena that can range from states of intolerance up to full-blown allergic reactions.

The presence of the alpha-Gal epitope in the milk, in addition to contributing apocrine secretion, is also influenced by the phenomenon of glycosylation of proteins.

Glycosylation means a post-translational modification of a protein, which sees sugars added to the peptidic chain.

Most of the proteins that are glycosylated in eukaryote cells are destined to become membrane proteins.

Allergy to the proteins of cow's milk is a far different condition from lactose intolerance, in that it is not a difficulty in digesting owing to an enzymatic deficit, but rather it is an actual immuno-mediated reaction aimed at the protein/glucose component, which is completely absent from or different in structure to human milk, and therefore foreign to our physiology.

The elimination diet, as with the subsequent therapeutic diet, entails the complete absence of such glycoproteins of cow's milk, and indeed of all foods that contain them, even in very low amounts (this is the case with many stuffed-meat products, various kinds of biscuits, many kinds of common bread, stock cubes etc.).

To this end, highly hydrolyzed types of milk or soy milk can be administered.

Recently a major link has emerged that correlates an anomalous over-expression of anti-alpha-Gal antibodies in highly-inflammatory forms of Inflammatory Bowel Diseases (IBDs). This group of diseases comprises illnesses like colitis, ulcerous rectocolitis and Crohn's disease. Significant correlations between circulating anti-alpha-Gal antibodies and the development of inflammatory diseases have also been highlighted for diseases like rheumatoid arthritis, eosinophilic esophagitis, and irritable colon syndrome (in general all the autoinflammatory forms that cause a variation of intestinal permeability). In all these cases, the ingestion of foods containing variable amounts of alpha-Gal epitope is potentially capable of further stimulating an already-over-loaded immune system, decisively contributing to aggravating the inflammatory state and favoring the chronicity of the disease.

The choice to develop an effective treatment capable of destroying the pro-allergenic properties of milk proteins/oligosaccharides is therefore urgent, indispensable and economically attractive.

The aim of the present invention is to provide a method for the inactivation and inactivation testing of xenoantigens in foods of vegetable and animal origin.

In particular, in this context, an object of the invention is to devise a method for the inactivation of the alpha-Gal epitope, in several kinds of milk.

Another object of the invention is to provide a method for inactivating the above mentioned epitopes, thus ensuring an effective clearance that can be applied to the different kinds of milk that are currently on the market.

Another object of the invention is to provide a method that can be carried out with conventional devices and machines.

This aim and these and other objects which will become better evident hereinafter are achieved by a method for the inactivation and inactivation testing of xenoantigens in foods of vegetable and animal origin, according to claim 1.

Further characteristics and advantages of the invention will become better apparent from the detailed description that follows of a preferred, but not exclusive, embodiment of the method according to the invention, the steps and outcomes of which are given, by way of non-limiting example, in the accompanying drawings, wherein.

DEFINITIONS

Figure 1:
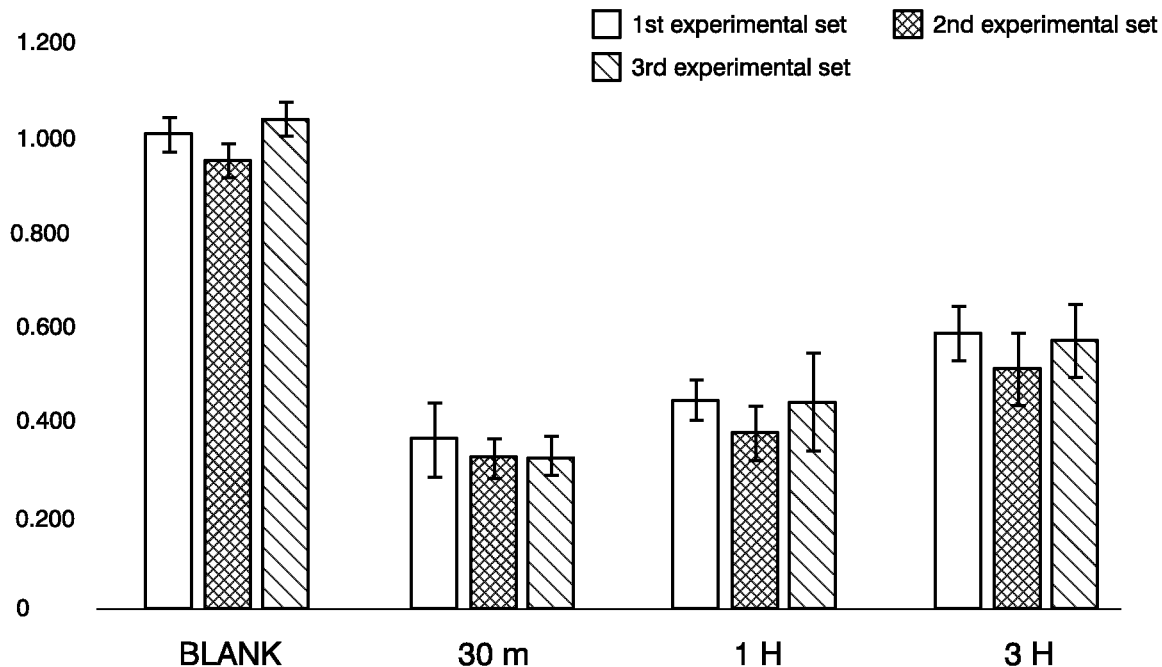
FIG. 1 is a first graph of the method according to the invention applied to a sample of a food treated with a vegetable extract titrated in verbascoside or an isoform thereof or a derivative thereof, at a first concentration.

The term "phenolic compounds" refers to molecules characterized, at least in part thereof, by the presence of an aromatic nucleus (benzene ring) bound to one or more hydroxyl functional groups.

The above mentioned compounds include, for the purposes of non-exclusive example:

simple phenols (molecules with a single benzene ring and containing only hydroxyl groups as substituents, e.g. phenol and hydroquinone), phenolic aldehydes (containing both the phenolic group and the aldehyde group, e.g. vanillin), phenolic acids (e.g. cinnamic acids), phenylamines (amphoteric molecules containing a weakly acidic group and a strongly basic group, e.g. phenylalanine), phenol compounds (the phenolic ring is bound to another benzene ring or to other heterocyclic compounds that have hydroxyl/lactone/ketone functional groups, e.g. coumarins and xanthones), flavonoids (made up of two benzene rings connected by a chain with three carbon atoms that constitutes an oxygenated heterocyclic ring, e.g. catechins, flavonons, flavones, chalcones, flavanonols, flavanols, leucoanthocyanidin, anthocyanin, anthocyanidin, proanthocyanidin and betalains), phenylpropanoids (characterized by the presence of an aromatic ring with an aliphatic side chain with three carbon atoms, es. hydroxycinnamic acids), tannins, porphyrins and carotenoids (carotenes and xanthophyll).

In the present invention the terms "phenols", "polyphenols" and "phenylpropanoids" have the same meaning and can be used individually, in the form of a mixture, or to substitute for each other for the set aims The term "xenoantigen" refers to molecules of animal origin that can be recognized by the immune system and can induce an antibody, immune-mediated, inflammatory or allergic response in the human host organism.

In the present invention the terms "xenoantigen", "antigen", "xenogeneic antigen", "epitope" and "determining antigenic" have the same meaning, and can be used together or to substitute for each other.

With reference to the figures, a method for the inactivation and inactivation testing of xenoantigens in foods of plant or animal origin is applied, by way of non-limiting example of the invention, to the inactivation of the alpha-Gal epitope from cow's milk, from soy milk and from rice milk.

Such method comprises the following steps:

making up a solution with a food of vegetable or animal origin as a solvent, for example cow's milk, or soy milk, or rice milk, and one or more phenolic compounds, polyphenolic compounds and derivatives thereof, comprising phenylpropanoids, hereinafter FPF, as a solute, for the inactivation of at least part of the xenogeneic epitopes from the food; the xenoantigen epitope is, in the present embodiment, the alpha-Gal epitope.

A vegetable extract with high content of phenylpropanoids, for the inactivation of at least part of the xenogeneic epitopes from the food, is constituted by vegetable extracts with a high content of one or both of verbascoside and teupolioside.

In particular, the phenolic compounds, polyphenolic compounds or derivatives thereof are constituted by vegetable extracts with high content of phenylpropanoids and in particular, by way of example, a vegetable extract titrated in verbascoside in the range between 50%-95%, the titration used for the examples of the invention is 93%, obtained from "Lippia citriodora" plants and a vegetable extract titrated in teupolioside in the range between 50%-85%, the titration used for the examples of the invention is 50%, obtained from "Ajuga reptans" plants in addition to phenyl derivatives of cinnamic acid, in particular caffeic acid, and of tannin, in particular tannic acid; in synthesis, such FPFs for the inactivation of at least part of the xenogeneic epitopes from the food, comprise: vegetable extracts titrated at 93% verbascoside, vegetable extracts titrated at 50% teupolioside, at least one phenyl derivative of cinnamic acid, at least one phenyl derivative of tannin;

incubating samples of milk with the addition of an antibody aimed at the alpha-Gal epitope that is present in the milk; in such embodiment, the antibody is for example a murine monoclonal antibody M86; it should be understood that all mono- or polyclonal antibodies and/or antibodies belonging to different isotypes, which have shown a proven specificity against the antigen in question, can be used; in general, the anti-xenoantigen antibody is an antibody specifically aimed at the alpha-Gal epitope;

separating, by way of centrifugation, the resulting immune complex created owing to the bond between antigen and antibody;

preparing a plate with 96 wells for the E.L.I.S.A. text with coating comprising the xenoantigen epitope, i.e. an alpha-Gal/human serum albumin coating;

adding, in the wells, supernatant taken from the milk samples subjected to centrifuge; the supernatant contains the part of anti-alpha-Gal antibody that has not bonded with epitopes; as is known, a column of wells is adapted to define a reference value, known in the jargon as 'blank value', that corresponds to the maximum signal between antibody and epitopes, completing the plate with a secondary antibody conjugated with an enzyme, or other molecule for qualitative or quantitative evaluation through colorimetric assay, adapted to chromatically highlight the presence if any of the anti-alpha-Gal antibody; in the present embodiment, the secondary antibody is constituted by a rabbit polyclonal anti-mouse antibody, conjugated with the peroxidase enzyme, or with other types, enzymatic or otherwise, capable of providing qualitative or quantitative indications through colorimetric assay;

reading the plate, determining the presence of anti-alpha-Gal antibody that has remained free in the solutions of the samples;

comparing the absorbance values detected in the column that defines the reference values with the values detected in the other columns of samples of the plate.

In particular, a first embodiment of such method for the inactivation of alpha-Gal epitopes in samples of cow's milk is described below in detail.

Two solutions are made up with different concentrations of phenylpropanoid, using the milk as solvent in a total volume of 50 ml. In this specific example, which obviously should be understood to be non-limiting of the invention, an extract of "Lippia Citriodora" was used, titrated at 93% verbascoside.

The different concentrations used for the preparation of the milk samples are: 0.01+/−0.005% and 0.005±0.002% w/v.

These solutions are left to act under moderate but constant stirring, for a total of 4±0.1 hours at 25±5° C.

Samples are taken at 30±2 minutes, 1±0.1 hour and 3±0.1 hours.

An aliquot of milk is taken from each sampling, comprised between 200 ul and 500 ul, and preferably 300 ul, to which a buffer is added, $Na_3C_6H_5O_7$ 0.2M at pH 7.0±0.5, until a final volume is reached comprised between 1000 ul and 1500 ul, and preferably a final volume of 1500 ul.

Then a murine antibody, directed against the alpha-Gal epitope, is added (in the present example this is an IgM clone called M86), at the preferable concentration of [1:50] w/v and the whole is incubated for 120±10 minutes at 37±2° C. under constant but moderate stirring.

At the end the samples are subjected to centrifugation at 10,000×g for 30±2 minutes at 4±2° C.

During incubation with the M86 antibody, a plate with 96 wells is prepared with 100 ul per well of alpha-Gal/HSA (Human Serum Albumin) at 5 ug/ml in a PBS buffer (pH 7.0±0.5).

The plate thus prepared is incubated for 60±10 minutes at a temperature comprised between 30° C.-40° C., although it is preferable to stabilize everything at 37° C.±2.0° C.

Then 3 washes are carried out with 300 ul per well of PBS (physiological pH) at ambient temperature.

The first wash is left to act for 5 minutes, the two subsequent washes for 3 minutes each.

The blocking is done with 300 ul per well of 2±0.5% of serum albumin in PBS, followed by covering the plate with protective film and incubation for 60±10 minutes at ambient temperature, in darkness.

Subsequently 3 washes are performed as above.

For each individual well, 100 ul of supernatant, taken from the treated samples after centrifugation, are added; the samples are loaded into the plate, each type of sample occupying at least 4 wells per column.

100 ul is loaded into the first column of the plate, taken from a batch constituted by an aliquot comprised between 1000 and 1500 ul of buffer (preferably a dose of 1500 ul is used) in which the aliquot of anti-alpha-Gal antibody is dissolved at the preferable concentration of [1:50] v/v without the presence of the sample of milk.

Such sample constitutes the reference value, also called "blank" value, and corresponds to the maximum bond on the plate between the anti-alpha-Gal antibody and alpha-Gal epitopes bonded to the HSA and exposed on the bottom of the wells.

Then the plate is covered with protective film and incubated at 37±2° C. for 120±10 minutes.

Then 3 washes with PBS are performed as above and 100 ul per well is added of a solution of secondary antibody (rabbit polyclonal anti-mouse) conjugated with peroxidase enzyme in phosphate buffer at pH 7.0±0.5 (the ideal solutions of such antibody have been found to be [1:1000], [1:500] and [1:100] v/v, preferably the intermediate one, [1:500] v/v, was adopted).

The plate is then covered again with protective film and incubated at 37±2° C. in darkness for 60±10 minutes.

Then 3 washes are performed as above.

Subsequently 100 ul is added per well of a development solution for the peroxidase enzyme, followed by covering the plate with protective film and incubation for 5±1 minutes in darkness.

Then 50 ul per well of the stop solution is added, which is constituted by $H_2SO_4$ 2M and the plate is then read in a plate reader at the wavelength of 450 nm.

The test of inactivation is based on the comparison between the absorbance values of the column that constitutes the blank value (100% of antibody available) and the respective columns of the samples.

If the absorbance (Abs) detected in the samples of treated milk corresponds to the Abs detected in the first column (blank batch), then it is possible to say that the anti-alpha-Gal antibodies left to incubate with the milk have not identified antigenic structures.

The unbound antibody was not able to create the interactions with the lipoprotein components of the milk that are responsible for the formation of the immune complex.

As a consequence, the unbound antibody was not sequestered by the centrifugation process, but instead remained free and available to interact with the alpha-Gal epitope bonded to the HSA and exposed on the bottom of the wells.

FIG. 1 shows a graph of the treatment of samples of cow's milk (three experimental sets, n=8 for each experimental set) with a vegetable extract titrated in verbascoside used at the concentration of 0.01% at ambient temperature (RT).

The vegetable extract administered at the concentration of 0.01% w/v has been found to be capable of inactivating 33.8±2.4% of the antigens after 30 minutes, 42.1±2.5% after 1 hour and 55.6±2.3% of the antigen after at least 3 hours of incubation.

Figure 2:
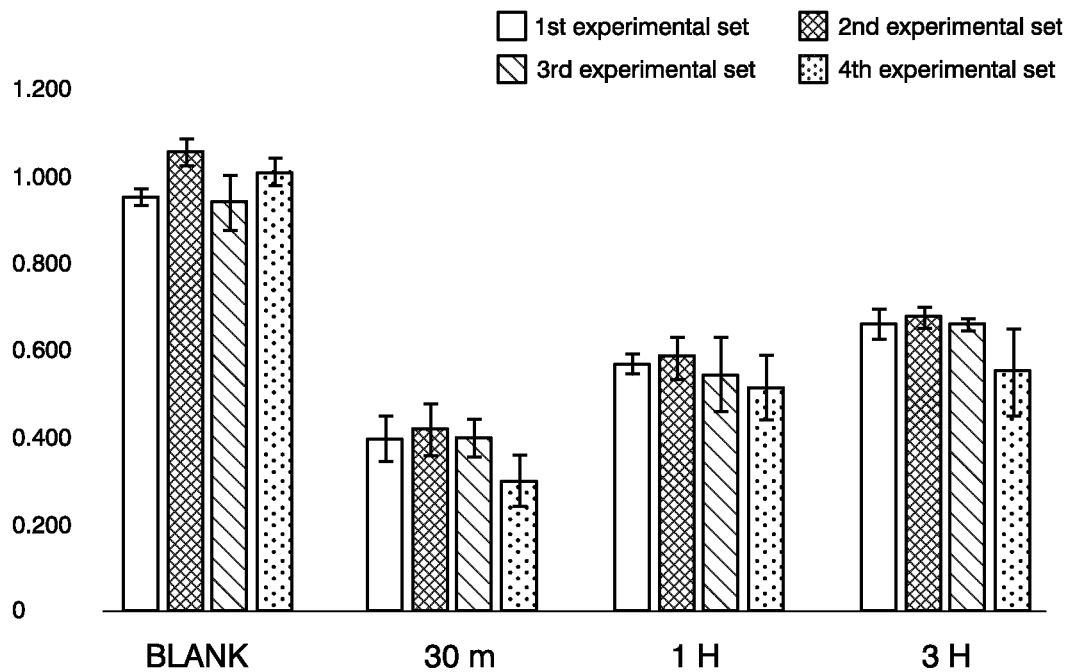
FIG. 2 is a second graph of the method according to the invention applied to a sample of a food treated with a vegetable extract titrated in verbascoside or an isoform thereof or a derivative thereof, at a second concentration.

FIG. 2 shows a graph of the treatment of samples of cow's milk (four experimental sets, n=8 for each experimental set) with a vegetable extract titrated in verbascoside used at the concentration of 0.005% at ambient temperature (RT).

The vegetable extract administered at the concentration of 0.005% w/v is capable of inactivating 38.2±5.9% of the antigens after 30 minutes, 55.8±3.7% of the antigens originally present after 1 hour of incubation, and reaches a percentage of 64.5±7.1 after at least 3 hours.

As a consequence, it has been found that this vegetable extract titrated at 93% verbascoside is effective if present in solution in amounts not lower than 0.005±0.001% w/v.

A second embodiment of the method according to the invention for the inactivation of alpha-Gal epitopes in samples of cow's milk, soy milk and rice milk is described below in detail, with the application of phenyl derivatives for the removal of the alpha-Gal epitopes in samples of full-fat cow's milk.

A solution is made up with a phenyl derivative of cinnamic acid, specifically with caffeic acid, using the milk as solvent in a total volume of 50 ml.

The preferable concentration to be used is 0.5±0.05% w/v.

The preparation is left to act under moderate but constant stirring, for a total of 4±0.1 hours at 25±5° C.

Samples are taken at 30±2 minutes, 1±0.1 hour and 3±0.1 hours.

An aliquot of milk is taken from each sampling, comprised between 200 ul and 500 ul, and preferably a dose of 300 ul, to which a buffer is added, $Na_3C_6H_5O_7$ 0.2M at pH 7.0±0.5, until a final volume is reached comprised between 1000 and 1500 ul, and preferably a final volume of 1500 ul.

Then a murine antibody, directed against the alpha-Gal epitope, is added (in this specific case an IgM clone called M86), at the concentration of [1:50] v/v and is left to incubate for 120±10 minutes at 37±2° C. under constant but moderate stirring.

At the end the samples are subjected to centrifugation at 10,000×g for 30±2 minutes at 4±2° C.

During incubation of the samples with the M86 antibody, a plate with 96 wells is prepared with 100 ul per well of alpha-Gal/HSA at 5 ug/ml in a PBS buffer (pH 7.0±0.5).

The plate is subsequently incubated for 60±10 minutes at a temperature comprised between 30° C.-40° C., although it is preferable to stabilize everything at 37° C.

Then 3 washes are carried out with 300 ul per well of sterile PBS (physiological pH) at ambient temperature.

The first wash is left to act for 5 minutes, the two subsequent washes for 3 minutes each.

The blocking is done with 300 ul per well of 2±0.5% of serum albumin in PBS and incubation for 60±10 minutes at ambient temperature, in darkness.

Subsequently 3 washes are performed as above.

For each individual well, 100 ul of supernatant, taken from the treated samples after centrifugation, are added, and the samples are loaded into the plate, each type of sample occupying at least four wells per column.

100 ul is loaded into the first column of the plate, taken from a batch constituted by an aliquot comprised between 1000 and 1500 ul of buffer (preferably a dose of 1500 ul is used) in which the aliquot of anti-alpha-Gal antibody is dissolved at the preferable concentration of [1:50] v/v without the presence of the sample of milk.

Such sample constitutes the reference value, also called "blank" value, and corresponds to the maximum bond on the plate between the anti-alpha-Gal antibody and alpha-Gal epitopes bonded to the HSA and exposed on the bottom of the wells.

Then the plate is covered with protective film and incubated at 37±2° C. for 120±10 minutes.

Then 3 washes with PBS are performed as above and 100 ul per well is added of a solution of secondary antibody (rabbit polyclonal anti-mouse) conjugated with peroxidase enzyme in phosphate buffer at pH 7.0±0.5 (the ideal solutions of such antibody have been found to be [1:1000], [1:500] and [1:100] v/v, preferably the intermediate one, [1:500] v/v, was adopted).

The plate is then covered again with protective film and incubated at 37±2° C. in darkness for 60±10 minutes.

Then 3 washes are performed as above.

Subsequently 100 ul is added per well of a development solution for the peroxidase enzyme, followed by covering the plate with protective film and incubation for 5±1 minutes in darkness.

Then 50 ul per well of the stop solution is added, which is constituted by $H_2SO_4$ 2M and the plate is then read in a plate reader at the wavelength of 450 nm.

If the absorbance detected in the samples of treated milk corresponds to the absorbance detected in the first column (blank batch), it means that the antibodies left to incubate with the milk have been recovered and consequently they have not identified antigenic structures. The unbound antibody was not able to create the interactions with the components of the milk that are responsible for the formation of the immune complex, and as a consequence it was not sequestered by the centrifugation process and it was recovered through the supernatant, going on to bond with the alpha-Gal antigen which is found processed together with the HSA on the bottom of the wells.

Figure 3:
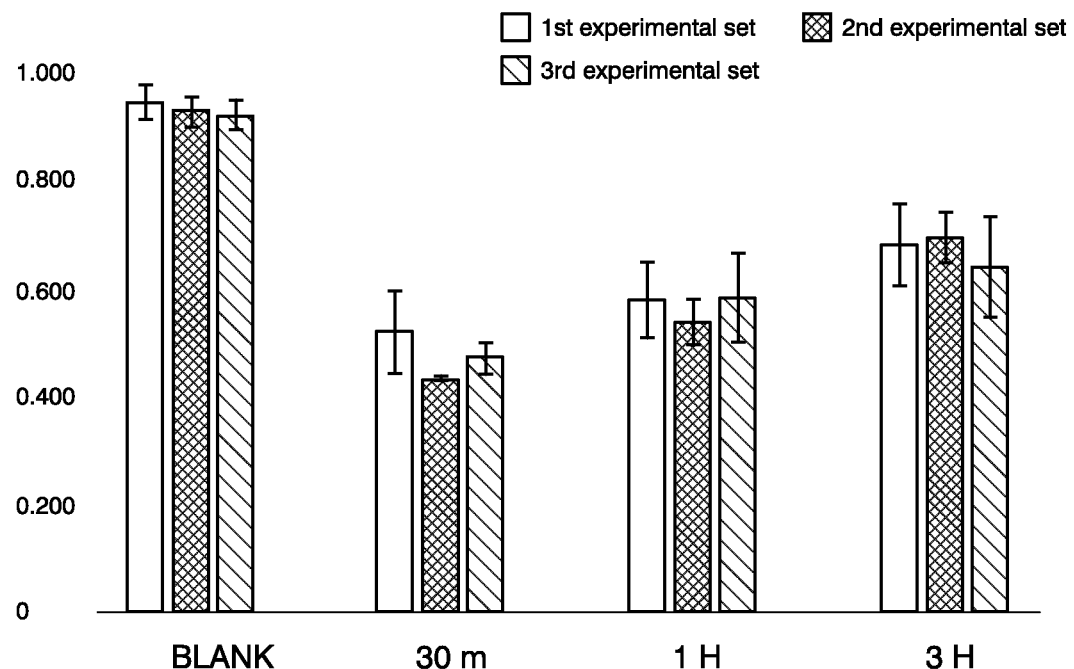
FIG. 3 is a graph of the method according to the invention applied to a sample of a food with a derivative of cinnamic acid.

FIG. 3 shows a graph of the treatment of samples of cow's milk (3 experimental sets, n=8 for each experimental set) with caffeic acid at the concentration of 0.5% w/v at ambient temperature (RT).

From the comparison with the blank column, it emerges that an inactivation of 51.2±4.2% of the antigens can be achieved after 30 minutes, of 61.1±2.6% after at least one hour of incubation, and this threshold rises to the percentage of 72.3±2.8% after 3 hours of incubation. Such treatment is optimal for a significant clearance of the treated milk.

A third embodiment of the method according to the invention for the inactivation of alpha-Gal epitopes in samples of cow's milk, soy milk and rice milk is described below in detail, with the application of phenyl derivatives for the removal of the alpha-Gal epitopes in samples of full-fat cow's milk.

Different solutions are made up with a phenyl derivative of tannin and with a phenylpropanoid, using the milk as solvent in a total volume of 50 ml. In this specific example, which obviously should be understood to be non-limiting of the invention, tannic acid and a vegetable extract of "Ajuga reptans" titrated at 50% teupolioside are used, and are preferably present in solution at the concentration of 0.5±0.05% w/v.

Preferably, the tannic acid is present in a solution at a concentration of 0.5±0.05% w/v. The preparation is left to act under moderate but constant stirring, for a total of 4±0.1 hours at 25±5° C.

Samples are taken at 30±2 minutes, 1±0.1 hour and 3±0.1 hours.

An aliquot of milk is taken from each sampling, comprised between 200 ul and 500 ul, and preferably a dose of 300 ul, to which a buffer is added, $Na_3C_6H_5O_7$ 0.2M at pH 7.0±0.5, until a final volume is reached comprised between 1000 and 1500 ul, and preferably a final volume of 1500 ul.

Then a murine antibody, directed against the alpha-Gal epitope, is added (in this specific case an IgM clone called M86), at the concentration of [1:50] v/v and is left to incubate for 120±10 minutes at 37±2° C. under constant but moderate stirring.

At the end the samples are subjected to centrifugation at 10,000×g for 30±2 minutes at 4±2° C.

During incubation of the samples with the M86 antibody, a plate with 96 wells is prepared with 100 ul per well of alpha-Gal/HSA at 5 ug/ml in a PBS buffer (pH 7.0±0.5).

The plate is subsequently incubated for 60±10 minutes at a temperature comprised between 30° C.-40° C., although it is preferable to stabilize everything at 37° C.

Then 3 washes are carried out with 300 ul per well of sterile PBS (physiological pH) at ambient temperature.

The first wash is left to act for 5 minutes, the two subsequent washes for 3 minutes each.

The blocking is done with 300 ul per well of 2±0.5% of serum albumin in PBS and incubation for 60±10 minutes at ambient temperature, in darkness. Subsequently 3 washes are performed as above.

For each individual well, 100 ul of supernatant, taken from the treated samples after centrifugation, are added, and the samples are loaded into the plate, each type of sample occupying at least four wells per column.

100 ul is loaded into the first column of the plate, taken from a batch constituted by an aliquot comprised between 1000 and 1500 ul of buffer (preferably a dose of 1500 ul is used) in which the aliquot of anti-alpha-Gal antibody is dissolved at the preferable concentration of [1:50] v/v without the presence of the sample of milk.

Such sample constitutes the reference value, also called "blank" value, and corresponds to the maximum bond on the plate between the anti-alpha-Gal antibody and alpha-Gal epitopes bonded to the HSA and exposed on the bottom of the wells.

Then the plate is covered with protective film and incubated at 37±2° C. for 120±10 minutes.

Then 3 washes with PBS are performed as above and 100 ul per well is added of a solution of secondary antibody (rabbit polyclonal anti-mouse) conjugated with peroxidase enzyme in phosphate buffer at pH 7.0±0.5 (the ideal solutions of such antibody have been found to be [1:1000], [1:500] and [1:100] v/v, preferably the intermediate one, [1:500] v/v, was adopted).

The plate is then covered again with protective film and incubated at 37±2° C. in darkness for 60±10 minutes.

Then 3 washes are performed as above.

Subsequently 100 ul is added per well of a development solution for the peroxidase enzyme, followed by covering the plate with protective film and incubation for 5±1 minutes in darkness.

Then 50 ul per well of the stop solution is added, which is constituted by $H_2SO_4$ 2M and the plate is then read in a plate reader at 450 nm.

If the absorbance detected in the samples of treated milk corresponds to the absorbance detected in the first column (blank batch), then we can say that the anti-alpha-Gal antibodies left to incubate with the milk have been recovered and consequently they have not identified antigenic structures. The unbound antibody was not able to create the interactions with the components of the milk that are responsible for the formation of the immune complex, and as a consequence it was not sequestered by the centrifugation process and it was recovered through the supernatant, going on to bond with the alpha-Gal antigen which is found processed together with the HSA on the bottom of the wells.

Figure 4:
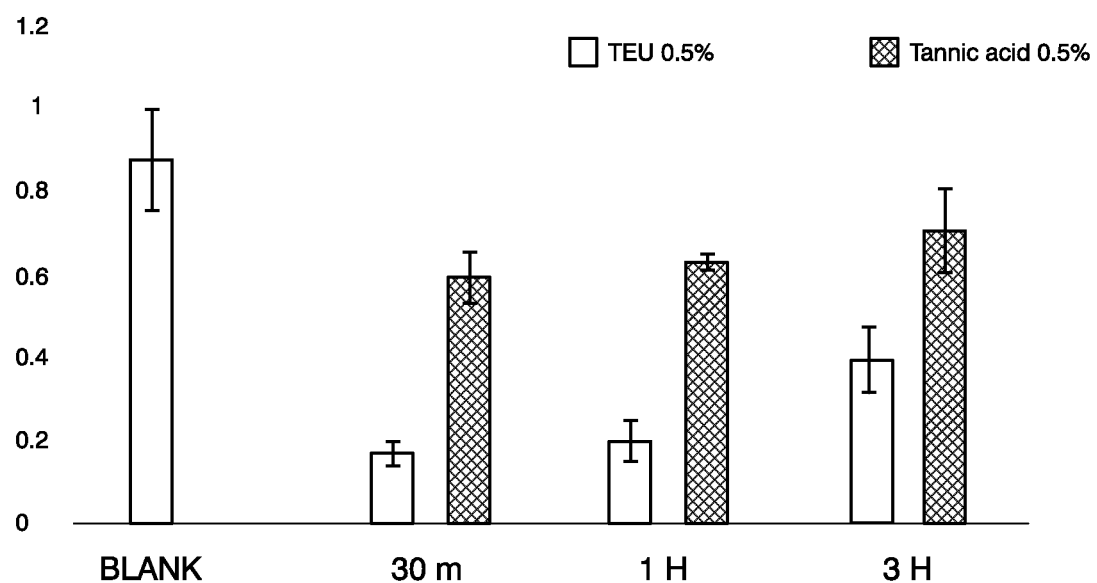
FIG. 4 is a graph of the method according to the invention applied to a sample of a food with a derivative of tannin or a vegetable extract titrated in teupolioside or an isoform thereof or a derivative thereof.

FIG. 4 shows a graph of the treatment of samples of cow's milk with a vegetable extract titrated in teupolioside and with tannic acid at the concentration of 0.5% w/v at ambient temperature (RT).

From comparison with the blank column, it can be seen that through the use of a vegetable extract titrated in teupolioside it is possible to achieve a limited capacity for inactivation of the alpha-Gal antigen equal to 19.1±1.5% after 30 minutes, to 22.6±1.1% after 1 hour and to 45.0±1.9% after 3 hours of incubation. The activity of the tannic acid has been shown to be capable of inactivating 67.7±7.1% of the antigens after 30 minutes, 71.8±2.2% after 1 hour and 80.6±1.8% after 3 hours of incubation.

The treatment of this food with such compounds has been shown to be capable of significantly lowering the reactivity of alpha-Gal epitopes, with a marked activity with reference to tannic acid.

A fourth embodiment of the method according to the invention for the inactivation of alpha-Gal epitopes in samples of cow's milk, soy milk and rice milk is described below in detail, with the application of plant cellular extracts with high content of phenylpropanoids, for example higher than 93%, and of their phenyl derivatives for the inactivation of the alpha-Gal epitopes in samples of milk substitutes based on rice and soya.

Three solutions are made up, using a milk substitute based on rice and soya as solvent, for example a substitute comprising 17% rice, 17% soy seeds, in a total volume of 50 ml.

In the present example, which is non-limiting of the invention, extracts of "Lippia citriodora" are used, titrated at 93% verbascoside.

The concentrations used for the preparation of the milk samples are: 0.01±0.005% w/v and 0.005±0.001% w/v. In addition a solution is made up of 0.5±0.05% w/v of a phenyl derivative of cinnamic acid, or of caffeic acid.

These solutions are left to act under moderate but constant stirring, for a total of 3±0.1 hours at 25±5° C.

Samples are taken at 30±2 minutes, 1±0.1 hour and 3±0.1 hours.

An aliquot of milk is taken from each sampling, comprised between 200 and 500 ul, and preferably a dose of 300 ul, to which a buffer is added, $Na_3C_6H_5O_7$ at pH 7.0±0.5, until a final volume is reached comprised between 1000 and 1500 ul, and preferably a final volume of 1500 ul.

Then a murine antibody, directed against the alpha-Gal epitope, is added, for example an IgM clone called M86, at the preferable concentration of [1:50] w/v and the whole is incubated for 120±10 minutes at 37±2° C. under constant but moderate stirring.

At the end the samples are subjected to centrifugation at 10,000×g for 30±2 minutes at 4±2° C.

During incubation with the M86 antibody, a plate with 96 wells is prepared with 100 ul per well of alpha-Gal/HSA (Human Serum Albumin) at 5 ug/ml in a PBS buffer (pH 7.0±0.5).

The plate thus prepared is incubated for 60±10 minutes at a temperature comprised between 30° C.-40° C., although it is preferable to stabilize everything at 37±2.0° C.

Then 3 washes are carried out with 300 ul per well of PBS (physiological pH) at ambient temperature.

The first wash is left to act for 5 minutes, the two subsequent washes for 3 minutes each.

The blocking is done with 300 ul per well of 2±0.5% of serum albumin in sterile PBS, followed by covering the plate with protective film and incubation for 60±10 minutes at ambient temperature, in darkness.

Subsequently 3 washes are performed as above.

For each individual well, 100 ul of supernatant, taken from the samples after centrifugation, are added.

The plate is loaded, each type of sample occupying at least 4 wells per column.

100 ul is loaded into the first column of the plate, taken from a batch constituted by an aliquot comprised between 1000 and 1500 ul of buffer (preferably a dose of 1500 ul is used) in which the aliquot of anti-alpha-Gal monoclonal antibody is dissolved at the preferable concentration of [1:50] v/v without the presence of the sample of milk.

Such sample constitutes the reference value, also called "blank" value, and corresponds to the maximum bond on the plate between the anti-alpha-Gal antibody and alpha-Gal epitopes bonded to the HSA and exposed on the bottom of the wells.

Then the plate is covered with protective film and incubated at 37±2° C. for 120±10 minutes.

Then 3 washes with PBS are performed as above and 100 ul per well is added of a solution of secondary antibody (for example, rabbit polyclonal anti-mouse) conjugated with peroxidase enzyme in phosphate buffer at pH 7.0±0.5; the ideal solutions of such antibody are [1:1000], [1:500] and [1:100] v/v, and preferably the intermediate one, [1:1000] v/v, is adopted.

The plate is covered again with protective film and incubated at 37±2° C. in darkness for 60±10 minutes.

Then 3 washes are performed as above.

Subsequently 100 ul is added per well of a development solution for the peroxidase enzyme, followed by covering the plate with protective film and incubation for 5±1 minutes in darkness.

Then 50 ul per well of the stop solution is added, which is constituted by $H_2SO_4$ 2M and the plate is then read in a plate reader at the wavelength of 450 nm.

The test of inactivation is based on the comparison between the absorbance values of column number 1 which constitutes the blank value (100% of antibody available) and the respective columns of the samples. If the Abs detected in the samples of treated milk corresponds to the Abs detected in the first column (blank batch), then we can say that the anti-alpha-Gal antibodies left to incubate with the milk have not identified antigenic structures.

The unbound antibody was not able to create the interactions with the lipoprotein components of the milk that are responsible for the formation of the immune complex.

As a consequence, it was not sequestered by the centrifugation process, but instead remained free and available to interact with the alpha-Gal epitope bonded to the HSA and exposed on the bottom of the wells.

Figure 5:
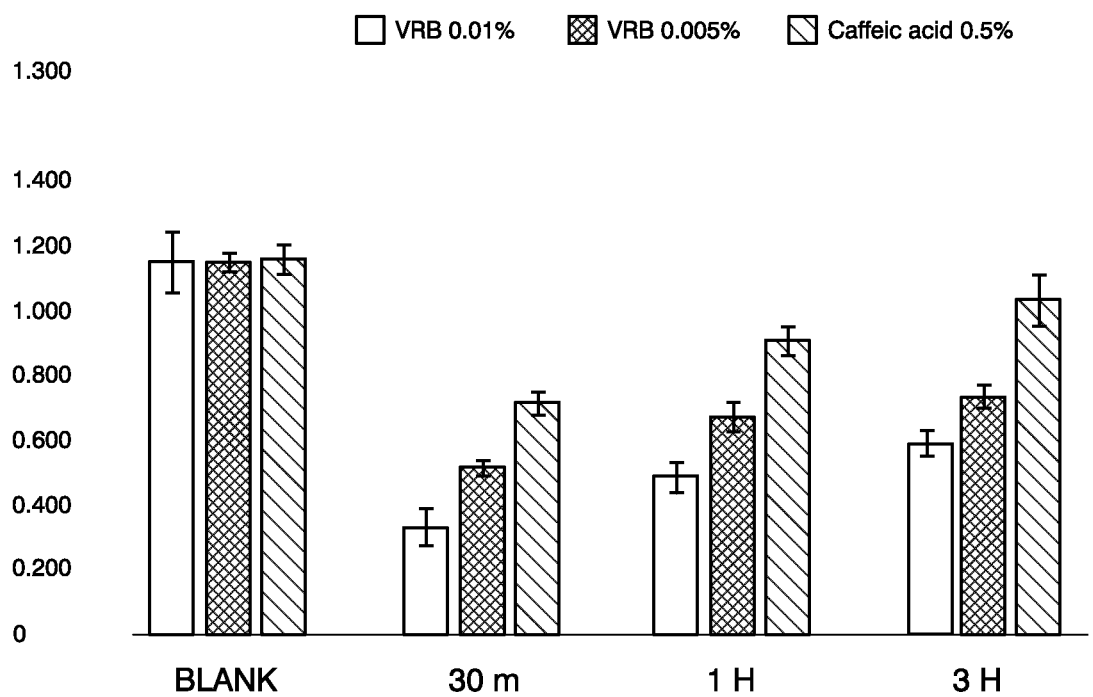
FIG. 5 is a graph of the method according to the invention applied to a sample of milk substitute, in particular soy milk and rice milk, treated with a vegetable extract titrated in verbascoside or an isoform thereof or a derivative thereof and a derivative of cinnamic acid.

FIG. 5 shows a graph of the treatment of samples of milk substitutes based on rice and soya with a vegetable extract titrated in verbascoside used at the concentration of 0.01% and 0.005% w/v and with caffeic acid 0.3% w/v (n=8 for each experimental set) at ambient temperature.

From comparison with the blank column, it can be seen that the treatment with a vegetable extract titrated in verbascoside and used at the concentration of 0.01±0.005% w/v has highlighted a limited capacity to inactivate 29.3±2.1% of the antigens after 30 minutes, 42.5±3.4% after 1 hour and 51.7±2.7% after 3 hours of incubation. The treatment with a vegetable extract titrated in verbascoside and used at the concentration of 0.005±0.001% w/v has highlighted an activity capable of inactivating 44.9±1.9% of the antigens after 30 minutes, 58.3±2.5% after 1 hour and 63.8±3.1% after 3 hours of incubation. The activity of the caffeic acid has been shown to be significantly more effective, and capable of inactivating 61.8±2.8% of the antigens after 30 minutes, 78.3±4.1% after 1 hour and 89.2±1.8% after 3 hours of incubation.

Such treatment is therefore effective for a significant clearance of milk substitutes based on rice and soya.

The invention also relates to a mixture of the above mentioned FPF compounds for the inactivation of at least part of the xenogeneic epitopes from these foods.

The invention also relates to a milk of animal origin, characterized in that at least part of the animal component constituted by the antigen in inactivated form is present.

In practice it has been found that the invention fully achieves the intended aim and objects.

In particular, with the invention a method has been devised for the inactivation and inactivation testing of the alpha-Gal epitope, in different kinds of milk.

Furthermore, with the invention a method has been devised for inactivating at least part of the above mentioned epitopes, thus ensuring a significant clearance that can be applied to the different kinds of milk that are currently on the market.

Last but not least, with the invention a method has been devised that can be carried out with conventional devices and machines.

The invention, thus conceived, is susceptible of numerous modifications and variations, all of which are within the scope of the appended claims. Moreover, all the details may be substituted by other, technically equivalent elements.

In practice the materials employed, provided they are compatible with the specific use, and the contingent dimensions and shapes, may be any according to requirements and to the state of the art.

The disclosures in Italian Patent Application No. 102016000115523 (UA2016A008267) from which this application claims priority are incorporated herein by reference.

The invention claimed is:

1. A method for alpha-Gal antigen intolerance mitigation, clearance, and testing in a food solution, comprising:
   providing a solvent comprising a food solution;
   inactivating at least a portion of alpha-Gal epitope in the food solution by:
   mixing a solute comprising at least one phenolic compound into the food solution to produce a food solution mixture, and
   stirring the food solution mixture, whereby the phenolic compound contacts alpha-Gal epitope to inactivate a portion of alpha-Gal epitope in the food solution mixture; and
   testing clearance of the alpha-Gal epitope in the food solution mixture by:
   sampling at least one aliquot of the food solution mixture, and
   measuring levels of alpha-Gal epitope.

2. The method of claim 1, wherein the food solution comprises a milk selected from: cows' milk, soy milk, or rice milk.

3. The method of claim 1, wherein the phenolic compound comprises at least one of verbascoside or teupolioside.

4. The method of claim 1, wherein the phenolic compound comprises verbascoside, wherein the verbascoside is provided as a plant extract containing verbascoside titrated in a range of 50% to 95%.

5. The method of claim 1, wherein the phenolic compound comprises verbascoside, wherein the verbascoside is provided as a plant extract containing verbascoside titrated in a range of 50% to 95%, and wherein the plant extract is present in the food solution mixture in a quantity not lower than 0.005±0.001% w/v.

6. The method of claim 1, wherein the phenolic compound comprises teupolioside, wherein the teupolioside is provided as a plant extract containing teupolioside titrated in a range of 50% to 85%.

7. The method of claim 1, wherein the phenolic compound comprises teupolioside, wherein the teupolioside is provided as a plant extract containing teupolioside titrated in a range of 50% to 85%, and wherein the plant extract is present in the food solution mixture at a concentration of 0.5±0.05% w/v.

8. The method of claim 1, wherein the phenolic compound comprises at least one of a phenyl derivative of cinnamic acid or a phenyl derivative of tannin.

9. The method of claim 8, wherein the phenyl derivative of cinnamic acid comprises caffeic acid.

10. The method of claim 9, wherein the caffeic acid is present in the food solution at a concentration of 0.5±0.05% w/v.

11. The method of claim 8, wherein the phenyl derivative of tannin comprises tannic acid.

12. The method according to claim 11, characterized in that said tannic acid is present in the food solution at a concentration of 0.5±0.05% w/v.

13. The method of claim 1, wherein the at least one phenolic compound comprises at least one of:
   a vegetable extract titrated in a range of 50% to 95% verbascoside,
   a vegetable extract titrated in a range of 50% to 85% teupolioside,
   at least one phenyl derivative of cinnamic acid, or
   at least one phenyl derivative of tannin.

14. The method of claim 1 wherein testing clearance of the alpha-Gal epitope comprises:
   incubating the aliquot with an anti-alpha-Gal antibody having binding affinity for alpha-Gal epitope, whereby the anti-alpha-Gal antibody binds with antigenic structures in the food solution mixture following the inactivating step,
   centrifuging the aliquot after the incubating step, producing a supernatant comprising unbound anti-alpha-Gal antibody, and whereby the supernatant is separated from bound anti-alpha-Gal antibody,
   loading the supernatant and a control onto a test plate comprising plate-bonded alpha-Gal epitopes, whereby unbound alpha-Gal antibody conjugates to the test plate comprising bonded alpha-Gal, and wherein the control defines a reference value that corresponds to the maximum signal between anti-alpha-Gal antibody and the plate-bonded alpha-Gal epitopes,
   developing and reading absorbance values on the test plate, and
   comparing absorbance values for the supernatant and the control, wherein the difference in absorbance values between the control and the supernatant indicates a measurement of alpha-Gal epitope in the food solution mixture.

15. The method of claim 1, wherein the phenolic compound comprises at least one of: a verbascoside, a teupolioside, a phenyl derivative of cinnamic acid, a phenyl derivative of tannin, a caffeic acid, or a tannic acid.

16. The method of claim 1, the phenolic compound comprises at least one of: a phenol, a hydroquinone, a cinnamic acid, a phenylalanine, a vanillin, a coumarin, a xanthone, a catechin, a flavonon, a flavone, a chalcone, a flavanonol, a flavanol, a leucoanthocyanidin, an anthocyanin, an anthocyanidin, a proanthocyanidin, a betalain, a hydroxycinnamic acids, a tannin, a porphyrin, a carotenoid, a carotene, a xanthophyll.

17. The method of claim 1, wherein the phenolic compound in the food solution mixture has a concentration in the food solution mixture of at least 0.005% w/v.

* * * * *